United States Patent
Heidrich et al.

(10) Patent No.: US 9,677,996 B2
(45) Date of Patent: Jun. 13, 2017

(54) OPTICAL SENSOR ARRANGEMENT INCLUDING DIFFERENT SCAN TIMES THROUGH A FREQUENCY INTERVAL FOR FIRST AND SECOND LIGHT SOURCES

(75) Inventors: Helmut Heidrich, Berlin (DE); Peter Lützow, Berlin (DE); Daniel Pergande, Berlin (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 437 days.

(21) Appl. No.: 14/345,812

(22) PCT Filed: Jun. 27, 2012

(86) PCT No.: PCT/EP2012/002737
§ 371 (c)(1),
(2), (4) Date: Jul. 15, 2014

(87) PCT Pub. No.: WO2013/041160
PCT Pub. Date: Mar. 28, 2013

(65) Prior Publication Data
US 2014/0326858 A1  Nov. 6, 2014

(30) Foreign Application Priority Data
Sep. 19, 2011  (EP) ..................................... 11075212

(51) Int. Cl.
*G01N 21/17* (2006.01)
*G01N 21/77* (2006.01)

(52) U.S. Cl.
CPC ......... *G01N 21/17* (2013.01); *G01N 21/7746* (2013.01); *G01N 2021/7723* (2013.01);
(Continued)

(58) Field of Classification Search
CPC ............... G01N 21/17; G01N 21/7746; G01N 2021/7776; G01N 2021/7723;
(Continued)

(56) References Cited

U.S. PATENT DOCUMENTS

| | | | |
|---|---|---|---|
| 5,448,657 A | * | 9/1995 | Kim ...................... G01D 5/344 372/6 |
| 6,721,053 B1 | | 4/2004 | Maseeh |

(Continued)

FOREIGN PATENT DOCUMENTS

| | | |
|---|---|---|
| EP | 2267432 A1 | 12/2010 |
| WO | WO02093221 A2 | 11/2002 |
| WO | WO2011000494 A1 | 1/2011 |

OTHER PUBLICATIONS

Braun, Ralf-Peter et al., "Optical Microwave Generation and transmission Experiments in the 12- and 60- GHz Region for Wireless Communications", IEEE Transactions on Microwave Theory and Techniques, vol. 46, No. 4, Apr. 1998, pp. 320-330.
(Continued)

*Primary Examiner* — Thanh Luu
*Assistant Examiner* — Jennifer Bennett
(74) *Attorney, Agent, or Firm* — Faegre Baker Daniels LLP (57) ABSTRACT

An optical sensor arrangement for measuring an observable including at least one light source for generating a first light component of a first frequency including a first mode and a second light component of a second frequency including a second mode orthogonal to the first mode, an optical resonator having differing optical lengths for the first and second modes, at least one of the optical lengths being variable depending on the observable and a dependence of the respective optical length being different for the first and second modes, and a detector unit coupled to the optical resonator for coupling out the two light components and
(Continued)

being configured for detecting a frequency difference between a resonance frequency of the optical resonator for the first mode and a resonance frequency of the optical resonator for the second mode.

12 Claims, 3 Drawing Sheets

(52) U.S. Cl.
CPC ............... *G01N 2021/7776* (2013.01); *G01N 2021/7789* (2013.01)

(58) Field of Classification Search
CPC ......... G01N 2021/7789; G01N 21/255; G01N 21/27; G02B 6/12; G02B 2006/12138; G02B 6/12004; G02B 6/2934; G02B 6/29338; G02B 6/29341; G02B 6/29343; G01J 1/04; G01J 1/42; G01J 3/26
USPC ....... 250/227.14, 216, 214 R, 227.19, 338.1; 356/73.1; 385/14
See application file for complete search history.

(56) References Cited

U.S. PATENT DOCUMENTS

| | | | |
|---|---|---|---|
| 7,796,262 | B1 | 9/2010 | Wang et al. |
| 7,903,906 | B2 | 3/2011 | Smith et al. |
| 2003/0189711 | A1* | 10/2003 | Orr ........................... G01J 3/42 356/484 |
| 2004/0023396 | A1 | 2/2004 | Boyd et al. |
| 2004/0146431 | A1 | 7/2004 | Scherer et al. |
| 2004/0190148 | A1 | 9/2004 | Clark et al. |
| 2005/0035278 | A1 | 2/2005 | Margalit et al. |
| 2006/0198415 | A1 | 9/2006 | Yamazaki |
| 2006/0227331 | A1 | 10/2006 | Vollmer et al. |
| 2010/0086261 | A1 | 4/2010 | Tanaka |
| 2012/0162659 | A1* | 6/2012 | Goldberg ........... G01N 21/4795 356/479 |
| 2014/0253917 | A1 | 9/2014 | Heidrich et al. |

OTHER PUBLICATIONS

Eisenhart, Robert L., "A Novel Wideband TM01-to-TE11 Mode Convertor", copyright 1998, IEEE, pp. 249-252.

Claes, Tom et al. "Vernier-cascade label-free biosensor with integrated arrayed waveguide grating for wavelength interrogation with low-cost broadband source", Optics Letters, vol. 36, No. 17, Sep. 1, 2011, pp. 3320-3322.

European Search Report issued in EP Application No. 11075212, dated Jan. 27, 2012, 11 pages.

European Search Report issued in EP Application No. 11075224, dated Mar. 15, 2012, 7 pages.

International Preliminary Report on Patentability, Chapter II, issued in PCT/EP2012/002737, completed Nov. 15, 2013, 24 pages.

International Search Report and Written Opinion issued in PCT/EP2012/002737, mailed Sep. 17, 2012, 13 pages.

International Search Report and Written Opinion issued in PCT/EP2012/004219, mailed Nov. 29, 2012, 10 pages.

Jin, Lei et al., "Optical Waveguide Double-Ring Sensor Using Intensity Interrogation With a Low-Cost Broadband Source", Optics Letters, vol. 36, No. 7, Apr. 1, 2011, pp. 1128-1130.

Lutzow, Peter et al., "Integrated Optical Sensor Platform for Multiparameter Bio-Chemical Analysis", Optics Express, vol. 19, No. 14, Jul. 4, 2011, pp. 13277-13284.

Mesaritakis, Charis et al., "Adaptive Interrogation for Fast Optical Sensing Based on Cascaded Micro-Ring Resonators", IEEE Sensors Journal, vol. 11, No. 7, Jul. 1, 2011, pp. 1595-1601.

Tamee, Kreangsak et al., "Distributed Sensors Using a Panda Ring Resonator type in Multiwavelenth Router", IEEE Sensors Journal, vol. 11, No. 9, Sep. 9, 2011, pp. 1987-1992.

International Preliminaiy Report on Patentability, issued in PCT/EP2012/004219, completed Jan. 14, 2014, 16 pages.

* cited by examiner

OPTICAL SENSOR ARRANGEMENT INCLUDING DIFFERENT SCAN TIMES THROUGH A FREQUENCY INTERVAL FOR FIRST AND SECOND LIGHT SOURCES

CROSS-REFERENCE TO RELATED APPLICATION

This application is a national phase application of PCT Application No. PCT/EP2012/002737, internationally filed Jun. 27, 2012, which claims priority to European Application No. 11 075 212.8, filed Sep. 19, 2011, both of which are herein incorporated by reference in their entirety.

TECHNICAL FIELD

The invention relates to an optical sensor arrangement for measuring an observable.

BACKGROUND

Optical resonators such as optical microrings are very sensitive optical sensor types that use the evanescent electromagnetic field travelling there through for scanning a surface. It is very difficult to produce multiple microrings with identical resonance properties, for example, the controlled spectral definition of a resonance peak with an accuracy in the picometer or sub-picometer region. One of the reasons why the production of identical microrings is so difficult is that the nanostructuring for producing said microrings is highly-dependent on the temperature dependency of the optical materials.

In order to scan resonance properties of different materials, passive reference resonators have been used. Examples for such resonators can be found in the document WO 2011/000494, where the reference resonators are actively controlled through a very sensitive temperature adjustment arrangement so that no or very small resonance shifts occur in the reference resonators. Said control units are very complex and not cost-efficient.

Document U.S. Pat. No. 7,903,906 B2 discloses an optical sensor arrangement for measuring an observable including at least one light source for generating a first light component of a first frequency comprising a first mode and a second light component of a second frequency comprising a second mode orthogonal to said first mode, an optical resonator having differing optical lengths for the first and second modes within a frequency interval including the first and second frequencies, at least one of the optical lengths being variable depending on the observable and a dependence of the respective optical length on the observable being different for said first and second modes. The at least one light source is optically coupled to the optical resonator for feeding the first and second light components into the optical resonators. Furthermore, a detector unit is present which is coupled to the optical resonator for coupling out the light components. Differences for each light component are measured in the presence of a substance and a resulting overall difference is calculated. Document US 2006/227331 discloses an optical sensor arrangement for measuring an observable comprising at least one light source for generating a first light component of a first frequency comprising a first mode and a second light component of a second frequency comprising a second mode orthogonal to said first mode. An optical ring resonator is present which has differing optical lengths for the first and second modes within a frequency interval. Furthermore, the light source is coupled to the optical resonator, and the optical resonator is coupled to a detector unit.

Similar devices are shown in documents US 2004/146431 and Peter Lützow et al., "Integrated optical sensor platform for multiparameter bio-chemical analysis", Optics Express, vol. 19, no. 14, 4 Jul. 2011.

SUMMARY

It is an objective technical problem to design an optical sensor arrangement for measuring an observable that is less complex than sensor arrangements found in the art and that may be used in a cost-efficient manner.

This disclosure relates to an optical sensor arrangement for measuring an observable utilizing at least one light source for generating a first and second light component of different modes, an optical resonator having differing optical lengths for the first and second modes, as well as a light source. In some embodiments, the light source and/or the optical resonator are tunable.

In some embodiments, the optical sensor arrangement for measuring an observable comprises at least one light source for generating a first light component of a first frequency comprising a first mode, the at least one light source also generating a second light component of a second frequency comprising a second mode orthogonal to the first mode.

Throughout this application, the term "orthogonal" is used in the quantum-mechanical sense, where different quantum states or different modes are said to be orthogonal if their representation in Hilbert space forms a subbasis of that Hilbert space. An example of said first and second modes would be the first and second polarizations of an electromagnetic wave such as a light wave. Another example would be the transversal modes of, e.g., a laser, where different TEM modes are orthogonal to each other and form at least a subbasis in the respective Hilbert space.

The first light component may comprise contributions from a mode different from the first mode. The same is true for the second light component, which may also comprise contributions from a first mode orthogonal to the second mode. It is, however, important that the first and second modes in the respective first and second light components are—at least in the Hilbert space—orthogonal to each other.

The first and second frequencies do not have to be equal but may differ from each other.

In some embodiments, the optical sensor arrangement for measuring an observable further comprises an optical resonator having differing optical lengths for the first and second modes within a frequency interval including the first and second frequencies, wherein at least one of the optical lengths is variable depending on the observable, and a dependence of the respective optical length is different for said first and second modes.

The optical length of an optical resonator is defined by its physical length multiplied by the refractive index of the material of said optical resonator. Optical resonators may have differing optical lengths for different modes such as polarizations, for example due to a rectangular cross-section of said optical resonator. The optical length relates to the resonance frequencies of the optical resonator through the relation $v = c \cdot k / A$, where c is the speed of light, k is a natural number between 1 and $\infty$, and where A denotes the optical length as defined above. The specific optical length has an influence on the first-order resonance frequency for k=1 as well as on all higher resonances for k=2, ..., $\infty$. In some embodiments, the optical resonator is configured such that the optical lengths for the first and second modes differ. While the physical length of the optical resonator might be identical for both modes, the refractive index n may differ due to asymmetries of the cross-section of the optical resonator.

In some embodiments, the optical resonator is designed such that at least one of the optical lengths is variable depending on the observable, such as pressure or temperature, or the presence or absence of molecules of a specific chemical compound. The dependence of the respective optical lengths of the first or second modes is different for each mode so that a shift in the optical length due to the observable has a different shift on the optical length for the first mode than on the optical length of the second mode.

In some embodiments, in order to measure the presence of the observable, the frequency interval is chosen or designed such that the first-order or any higher order resonance frequency of the optical length when the observable is not present and the resonance frequency connected with the optical lengths of the presence of the observable are included in the frequency interval. As the resonance frequencies or optical lengths, respectively, are different depending on whether the observable is or is not present, the frequency difference between the first and second modes is also different depending on the observable's presence. Hence, said optical sensor arrangement may be used for measuring frequency differences in order to measure the presence of an observable.

While we have described the frequency interval only in terms of the first-order resonance frequencies independent of the optical lengths, it is well within the scope of the present disclosure for the frequency interval to span higher-order resonances in connection with first-order resonances or resonances of any other order.

In some embodiments, as the optical length of the optical resonator is different for the first and second modes and changes due to the observable, the at least one light source and/or the optical resonator are tunable within said frequency interval such that the different resonance frequencies of the optical resonators may be scanned to produce a signal in the detector unit.

In some embodiments, this detector unit is coupled to the optical resonator and is generally configured for detecting a frequency difference between a resonance frequency of the optical resonator for the first mode and a resonance frequency of the optical resonator for the second mode.

In some embodiments, the detector unit may comprise optoelectronic elements, such as photodiodes, and electronic equipment, such as an optional power spectrometer or an intensity spectrometer. The output signal of the photo detector can be configured to show a signal with a beat frequency of a superposed optical signal stemming from the first and second light sources. The electronic spectrometer is preferably attached to the output of the photo detector and transfers the output signal of the photo detector from the time domain to the frequency domain.

In some embodiments, the detector unit may comprise its own processing unit or may be connected to a computer for analyzing the data detected by the detector unit.

In some embodiments of the optical sensor arrangement, the at least one light source comprises a first light source for generating the first light component and a second light source for generating the second light component, the first and second light sources being coupled to the optical resonator and being tunable independently of each other.

Using two separate light sources for generating the first and second components is advantageous as the different light sources may be tuned independently of each other such that the first and second light sources can produce light of different frequencies at the same time. Consequently, this has the effect that the different resonance frequencies caused by the different optical lengths of the optical resonator may be scanned simultaneously, hence, scanning through the entire or pans of the frequency interval is accelerated.

In some embodiments, the optical sensor arrangement including first and second light sources comprises a control unit for the at least first and second light sources and/or for controlling the optical resonator, wherein the control unit preferably tunes the at least one light source through said frequency interval or tunes the optical resonator through said frequency interval in the case of a control unit for a tunable light source, the control unit may tune the resonator chamber of, for example, a laser. In the case of a tunable optical resonator, the control mechanism depends on the resonators used. For example, when a Fabry-Perot resonator is used, the distance between two mirrors may be changed to control the different optical lengths. In the case of micro-optic ring resonators (microrings), the control unit may apply pressure or temperature or any other suitable observable to the ring resonator so that said observable changes the optical length and thus tunes the optical resonator through said frequency interval.

In some embodiments, the scan time for scanning through said frequency interval is different for the first and second light sources, and the scan time of the first light source is a multiple of the scan time of the second light source, by a factor of more than five.

In some embodiments, when scanning through the frequency interval from its lower boundary to its upper boundary, the first light source, for example, may increase the frequency linearly from the lower to the upper boundary.

In some embodiments, at the same time, the control unit controls the second light source such that the frequency interval is scanned at a much faster rate, for example 10 times as fast. When the upper boundary is reached, the frequency of the second light source is tuned down to the lower boundary and the control unit scans the frequency interval again. In total, this results in the frequency interval being scanned by the first light source once while being scanned by the second light source ten times. This has the effect that at some time during the scan the differing first and second resonance frequencies for the first and second modes are scanned simultaneously.

In some embodiments, the optical sensor arrangement comprises a mode converter arrangement that is situated between the optical resonator and the detector unit. In particular, the mode converter arrangement may be configured to "rotate" the first and/or second modes such that both modes comprise components in a matching transversal direction. In the case of the modes being different transversal polarizations of light, the mode converter arrangement may comprise a polarization rotator in the form of lambda platelets or similar devices for rotating a polarization from a first mode perpendicular to a second mode into the direction of the second mode. As mentioned before, the rotation in this application is generalized towards a rotation in the corresponding Hilbert space of the modes.

In some embodiments, by rotating the first and second modes such that the modes are no longer perpendicular to each other but parallel to each other, the modes may be mixed, and by using a corresponding detector unit, the frequency difference to be measured can be detected by analyzing the beat of the superposed first and second light components now comprising components in matching directions, such that the beat is determined by the absolute value of the difference of the first and second frequencies. This is advantageous because for first and second frequencies that are very close to each other, the beat is a much slower variation of the superposed signal and may be detected by electronic components, thus simplifying the optical sensor arrangement and allowing for the detection of resonances that are situated very closely to each other. Essentially, very small variations of an observable may be detected. The output signal of the detector unit may be used as a direct qualitative or quantitative measure for the presence of the observable, i.e., pressure, temperature, presence of molecules or DNA or the like. As measurements conducted through electronic components are more accurate than measurements made by optoelectronic components due to the electronic filtering characteristics, a better signal resolution may be achieved.

In some embodiments, the mode converter arrangement may comprise not only a polarization rotator but also a polarization splitter for decoupling the first and second modes.

In some embodiments where the first and second modes are orthogonal TEM modes of light, the mode converter arrangement may comprise a mode converter that may be realized, for example, through the variation of the cross-section of an optical wire.

In some embodiments, the optical resonator is at least partially covered with an active layer of covering material for selectively absorbing a group of substances comprising a substance to be detected and wherein the covering material is configured such that at least one of the resonance frequencies of the optical resonator is shifted when the substance contacts the active layer. The active layer may be used for selectively accumulating molecules of the substance to be detected. An optical sensor arrangement comprising said active layer may be easily used as a e.g. biosensor for measuring the presence of a group of substances (i.e. an observable) since the differences in resonance frequencies for the first and second modes, due to the presence or absence of a member of the group of substances, can be easily detected.

In some embodiments, the application of an active layer has the advantage that since both the first and second light components are coupled into the same optical resonator, a reference resonator is no longer necessary because the differences in resonance frequencies can be measured by a single optical resonator. While more than one optical resonator may be coupled to the arrangement, it is to be noted that both the first and second light components have to be fed through the same resonator.

In some embodiments, the at least one light source is coupled to the optical resonator through at least one optical path comprising an optical waveguide given, for example, by ribs or by doping of regions forming a waveguide in semiconductor materials. The optical resonators may be provided on the same substrate connected to the waveguide, such that the evanescent field of the waveguide feeds light coming from the light source into the optical resonator and from there to the detector unit or, optionally, the mode converter arrangement.

In some embodiments, a coupler is situated before and/or behind the optical resonator. When different light sources are used, the setup of the optical sensor arrangement may be simplified by coupling light, for example, through a Mach-Zehnder interferometer. The coupler has the effect that after the coupling only a single optical waveguide carrying both the first and second light components is necessary. This further miniaturizes the optical sensor arrangement.

In some embodiments, the at least one light source may comprise a laser. In the case of differing first and second light sources, a first and a second laser tunable independently of each other may be used. The first and second lasers may be used as single mode slave lasers that differ in their emission wavelength and that are synchronized via "injection-locking" such that the noise in the phase of the emitted light is synchronized. Regarding "injection-locking", reference is made to R.-P. Braun et al., "Optical Microwave Generation and Transmission Experiments in the 12- and 60-GHz Region for Wireless Communications", IEEE TRANSACTIONS ON MICROWAVE THEORY AND TECHNIQUES, vol. 46, no. 4, pages 320-329, 1998. The slave lasers are driven by a single mode master injection laser. In some embodiments, comprising two slave lasers has the advantage that the width of the intermediate frequency (between the first and second resonance frequencies) may be reduced into the Hertz region, thus resulting in a simple setup with a high resolution.

The disclosure further comprises a method for measuring an observable by means of an optical sensor arrangement. In some embodiments, the method comprising coupling light of a first frequency comprising a first mode into an optical resonator and coupling light of a second frequency comprising a second mode into the optical resonator, wherein the second mode is orthogonal to the first mode and the optical resonator has differing optical lengths for the first and second modes within a frequency interval including the first and second frequencies and at least one of the optical lengths is variable depending on an observable and a dependence of the respective optical length on the observable is different for the two different modes. Regarding details of this method, reference is made to the foregoing sections.

Further details regarding an optical sensor arrangement according to the disclosure can be found in the drawings. It is pointed out that features not claimed in the independent or dependent claims but shown in the drawings are, each in its own right, also features without necessarily including all further features shown in a single Figure depicting an arrangement or discussed in the description of the respective arrangement. Consequently, any single feature shown in a specific arrangement may be claimed individually. In particular, features described in connection with the optical sensor arrangement may be claimed for the disclosed method and vice versa.

BRIEF DESCRIPTION OF THE DRAWINGS

The embodiments of the disclosure are subsequently explained with reference to FIGS. 1-4.

DETAILED DESCRIPTION

Figure 1A:
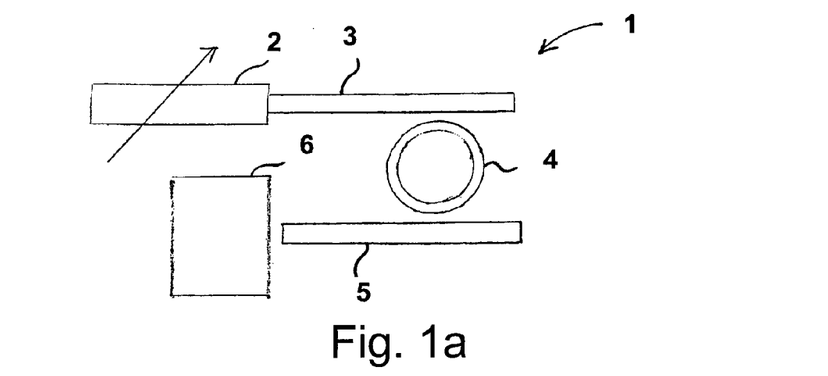
FIGS. 1a and 1b are diagrams illustrating an optical sensor arrangement and the respective intensity spectrogram due to the different optical lengths of an optical resonator, according to some embodiments of the disclosure.

FIG. 1a is a diagram illustrating an optical sensor arrangement 1 according to a first aspect of the disclosure. The optical sensor arrangement 1 comprises a tunable laser 2 for generating a first light component comprising a first mode and a second light component comprising a second mode. In some embodiments, both components are generated simultaneously. The first light component comprising the first mode relates to the horizontal transversal polarization of the electromagnetic wave, while the second light component is vertically polarized and thus defines the second mode. Both the first light component and the second light component are of the same frequency because the tunable laser emits the light of said frequency. Consequently, the first and second light components are coupled due to their generation within a single laser.

The tunable laser 2 is coupled to an optical wire 3 that may be embodied by a rib made of silicon on a silicon substrate. It may be buffered through a $SiO_x$ layer. Various other materials may be used for producing such optical wires. The optical wire 3 transmits the first and second light component generated by tunable laser 2 and runs by an optical ring resonator 4 that is a closed silicon ring on a silicon substrate. As the distance between the optical wire 3 and the optical ring resonator 4 is chosen such that the light components transmitted by the optical wire 3 may couple through their evanescent fields with the optical ring resonator, the first and second light components are transmitted into the optical ring resonator.

Optical ring resonator 4 has an optical length defined by its physical length and the effective refractive optical index of the material of which the resonator is made. In the present case, the optical ring resonator 4 has different optical lengths for the first and second modes within a frequency interval through which the tunable laser 2 may be tuned. Hence, as the optical lengths of the optical resonator differ for the first and second modes, different resonant frequencies are detected in the optical resonator. Only resonant frequencies may pass through the optical ring resonator and may re-couple into optical wire 5, which transmits the light of a resonant frequency into detector unit 6.

In addition to having differing optical lengths for the first and second modes within said frequency interval, optical resonator 4 is covered with an active layer of covering material for selectively adsorbing a group of substances comprising a substance to be detected. When a substance contacts the active layer, the optical length of the resonator for the first and/or second mode is shifted. In the example, both the optical lengths for the first and for the second mode are shifted.

Figure 1B:
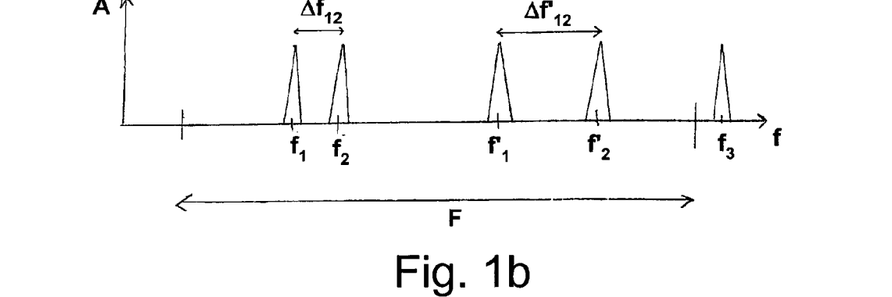

For illustration of this principle, the reader is referred to FIG. 1b, wherein frequency F is marked on the x-axis and intensity A on the y-axis. The intensity A is proportional to the squared value of the amplitude of the emitted first and second light components.

The tunable laser 2 may be tuned within the frequency interval F. Within the interval, resonance frequency $f_1$ refers to the resonance of the optical ring resonator when no substance is in contact with the active layer, while $f_2$ is the resonance frequency for the second mode of the optical ring resonator when no substance contacts the active layer. The difference $\Delta f_{12}$ is also shown.

When the tunable laser 2 is tuned throughout the frequency interval F, the first light component is coupled into optical wire 5 when the frequency is $f_1$. In a similar fashion, the second light component is coupled into the optical wire 5 when the tunable laser is tuned to frequency $f_2$.

In the presence of a substance contacting the active layer, the optical lengths for the optical resonator are shifted from $f_1$ to $f'_1$ and from $f_2$ to $f'_2$, respectively. It can be easily seen that the difference $\Delta f_{12}$ is different from $\Delta f'_{12}$.

A higher-mode resonance frequency $f_3$ of the optical lengths is also shown in FIG. 1b in order to illustrate that resonance frequencies are not scanned by the tunable laser when they are outside the chosen frequency interval.

Detector unit 6 is equipped with, for example, photo detectors or electronic spectrometers to measure the light intensity throughout the frequency interval. The detector unit, for example comprising photo detectors, measures an intensity of 0 when the frequency of the tunable laser is outside a narrow gap between the resonance frequencies $f_1$, $f_2$, $f'_1$, and $f'_2$. When the intensity curves as shown in FIG. 1b are found, one can easily indentify from the difference between the resonance frequencies detected by the detector unit whether the substance is present on the active layer of the optical resonator 4 or not. It should be noted that even though FIG. 1b displays both resonance frequency differences (with and without the chosen substance present on the active layer, such as a particular molecule or DNA snippet), usually only one of the two shown differences will be measurable under working conditions. When the optical circuit of the optical sensor arrangement 1 is produced and one is certain that no substance has contacted the active layer, the difference in the resonance frequencies $f_1$ and $f_2$ should be determined.

Figure 2A:
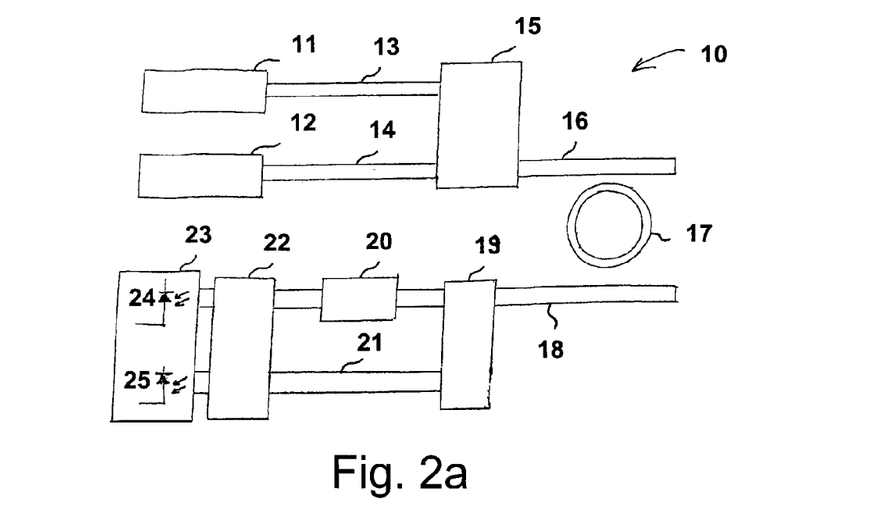
FIGS. 2a through 2c are diagrams illustrating an optical sensor arrangement and the detection of a frequency difference by superposing the first and second light components after their having passed through the optical resonator by analyzing the beat of the superposed light components, according to some embodiments of the disclosure.

FIG. 2a is a diagram illustrating an optical sensor arrangement 10, according to some embodiments. Optical sensor arrangement 10 comprises a first tunable laser 11 and a second tunable laser 12, which are coupled through optical wires 13 and 14 and are transmitted to an optical coupler 15, which leads to a superposing of the first and second light components each emitted by the first and second tunable lasers 11 and 12, respectively, through an overlap of the evanescent fields of the emitted light waves. The superposed wave is then transmitted through an optical wire 16 and coupled into an optical ring resonator 17 that is comparable to the optical ring resonator 4.

In contrast to the arrangement shown in FIG. 1a, the arrangement of FIG. 2a comprises two tunable lasers, so that the first and second light components emitted at a first and second frequency may have different frequencies at the same time. Hence, in contrast to the arrangement shown in FIG. 1a, it is possible to scan through several resonances at the same time. Referring back to FIG. 1b, it is thus possible to scan resonance frequency $f_1$ of the first mode emitted by the first tunable laser 11 at the same as the second resonance frequency $f_2$ of the second mode emitted by the second tunable laser 12. Similarly, when a substance is contacting the active layer of the optical resonator 17 (not shown), the detectable resonance frequencies $f'_1$ and $f'_2$ may also be detected at the same time.

Figure 2B:
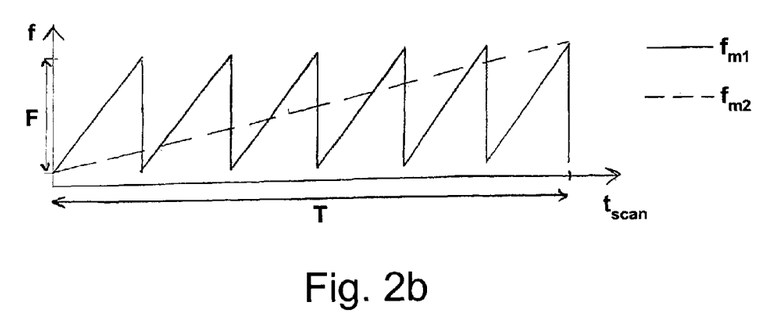

FIG. 2b is a diagram illustrating a scanning scheme, according to some embodiments of the disclosure. The x-axis shows the scan time. Within a scan time interval of T, tunable laser 11, emitting a first light component at a first frequency $f_{m1}$, scans through the frequency interval F six times. During the scan time T the tunable laser 12, emitting a second light component at the second frequency $f_{m2}$, scans through the frequency interval only once. This scheme may be used in such a manner that every combination of frequencies $f_{11}$, $f_{12}$ is scanned, which makes it possible to scan resonance frequencies $f_1$ and $f_2$ as shown in FIG. 1$b$ at the same time.

In the following, it is assumed that the first light component frequency $f_{m1}$ is tuned to the resonance frequency $f_1$ and the frequency of the second light component $f_{m2}$ is tuned to the resonance frequency $f_2$. As both these frequencies are resonant within the optical resonator 17, they are both emitted into the optical wire 18. They are transferred to a polarization splitter 19 that splits the horizontal and vertical polarizations. Assuming that the horizontal polarization light component is fed into the upper optical wire comprising the polarization rotator 20, for example in the form of a lambda platelet, and that the horizontal polarization light component is fed to/into the lower optical wire 21, the polarization rotator 20 rotates the vertical polarization to a horizontal polarization and ultimately both light components have the same polarization and may be superposed in the optical coupler 22.

Due to the coupling of light of different frequencies of the same polarization, the superposed wave is made of two different frequency components. The first frequency component is the sum of the frequencies $f_1$ and $f_2$. The second frequency component is the difference between frequencies $f_1$ and $f_2$ and results in a modulation of the amplitude of the superposed wave.

Figure 2C:
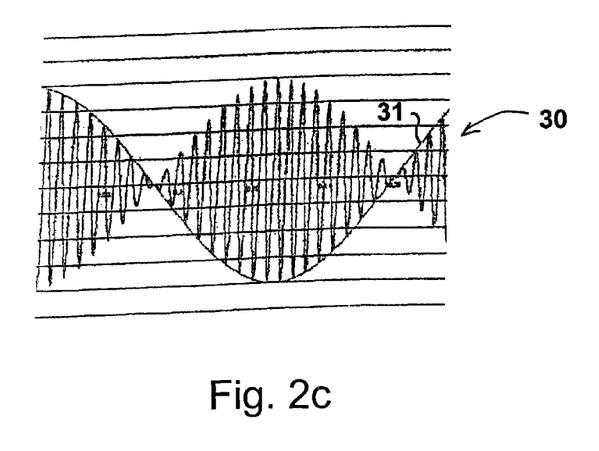

FIG. 2$c$ is a diagram illustrating the modulation, according to some embodiments of the disclosure. The superposed wave 30 shows a modulation 31 of the amplitude, generally known as the "beat" of the superposed wave. The envelope has a frequency of $f_1$-$f_2$. The frequency of the beat may thus allow a user to determine whether a substance is present due to difference between $\Delta f_{12}$ and $\Delta f'_{12}$. The frequency of the beat is much slower than the frequency of the optical wave and the photo detectors 24 and 25 of the detector unit 23 may measure the amplitude modulation and transfer the amplitude modulation to an electronic spectrometer, as the difference in frequencies of the optical waves is slow enough to be detected by electronic components. Hence, via means such as electronic spectrometers, it is possible to detect small frequency differences of resonances indicative of whether a substance, i.e., an observable, is located on the active layer of an optical resonator. The arrangement of FIG. 2$a$ is thereby able to detect a shift in optical lengths or resonance frequencies of the optical resonators in the region of less than 0.1 picometers, in the optical spectral interval around 1.5 micrometers. Hence, the arrangement of FIG. 2$a$ is suited for providing a very sensitive sensor for measuring whether a substance is present or not.

Figure 3:
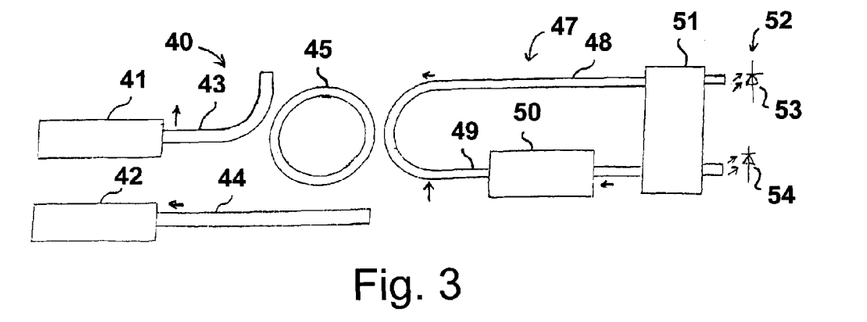
FIG. 3 is a diagram illustrating an optical sensor arrangement, according to some embodiments of the disclosure.

FIG. 3 is a diagram illustrating an optical sensor arrangement, according to some embodiments of the disclosure. Optical sensor arrangement 40 comprises first and second tunable lasers 41 and 42 coupling to optical wires 43 and 44, respectively. Both lasers 41 and 42 emit transversally polarized light, a second light component emitted by the second laser 42 being polarized orthogonal to a first light component emitted by the first laser 41. Both light components or modes are coupled into the ring resonator 45, light emitted by the first laser 41 propagating clockwise and light emitted by the second laser 42 propagating counter-clockwise. From the ring resonator 45, the two modes are transmitted to the optical wire arrangement 47, which comprises a first branch 48 of an optical wire for the light component emitted by the second laser 42 and a second branch 49 for the light component emitted by the first laser 41. The second branch 49 comprises a polarization rotator 50 that may shift the polarization of the light emitted by the first laser 41 to be parallel to the polarization of the light of the second laser 42. Once the polarization of the first light component has been switched to the other polarization, both components are superposed in coupler 51 and transferred to detector unit 52 comprising photodiodes 53 and 54, both of which are coupled to a digital amplifier and an electronic spectrometer. In a similar fashion as the arrangement of FIG. 2$a$, the arrangement of FIG. 3 may be used to detect minuscule resonance shifts that are due to the presence of an observable on an active layer of the ring resonator 45 suited for being contacted by biomolecules or fluids or other substances or observables to be detected. This is due to the fact that the ring resonator 45 has at least slightly different optical lengths for the two modes, the optical length for the mode emitted by the first laser 41 depending more sensitive on the respective observable than the optical length for the mode emitted by the second laser 42.

Figure 4:
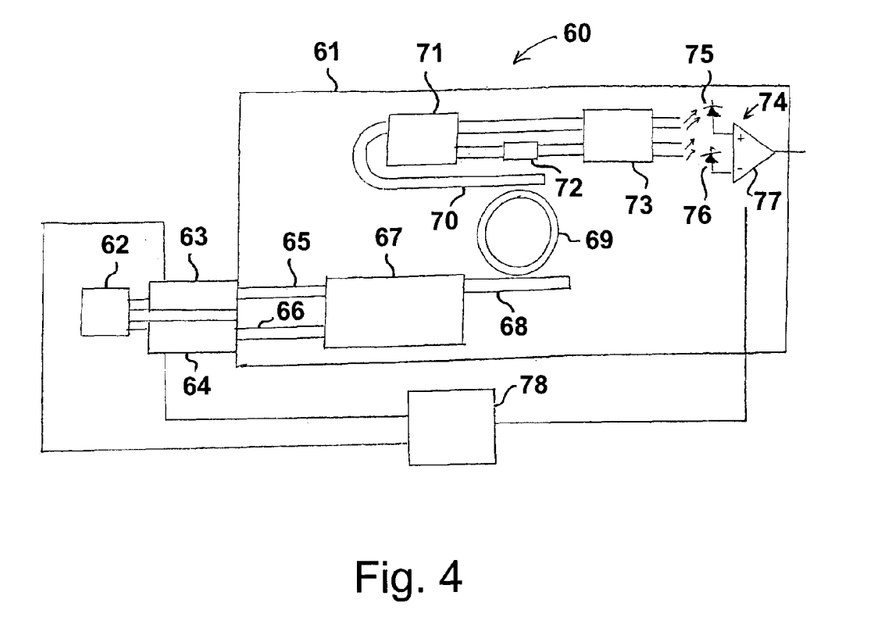
FIG. 4 is a diagram illustrating an optical sensor arrangement on a silicon substrate, according to some embodiments of the disclosure.

FIG. 4 is a diagram illustrating an optical sensor arrangement 60, according to some embodiments of the disclosure. Optical sensor arrangement 60 is situated on a silicon substrate 61. In contrast to the arrangements shown in FIGS. 2$a$ and 3, the optical arrangement 60 comprises a master laser 62 coupled to two single-mode slave lasers 63 and 64 that are different in their emission wavelength and synchronized via injection locking, i.e., the phase noise is synchronized between the two slave lasers. By using this tunable source with synchronized phase noise, the width of the frequency difference may be reduced to be in the Hertz region, and thus a high resolution for detecting resonance shifts or the presence of an observable on an optical resonator is given.

Despite the different laser arrangements, optical sensor arrangement 60 is similar to the arrangement of FIG. 2$a$. In particular, light from the tunable lasers is coupled via optical wires 65 and 66 into an optical coupler 67, then to an optical wire 68 and into the optical ring resonator 69 comprising an active layer, then into the optical wire 70, the different polarizations emitted by the first and second laser 63 and 64 being separated in the polarization splitter 71, the polarization of one of the components being rotated in the polarization rotator 72, and the two remaining waves being superposed in coupler 73. Detector unit 74 comprises photodiodes 75 and 76, both of which are connected to a digital amplifier 77.

In a variation of the optical sensor arrangement 60, both lasers 63 and 64 may be configured such that they emit different TEM modes. One of the lasers 63 emits a TEM mode 01 while the other emits a TEM mode 11. Both lasers are tuned via a control unit 78, which may also receive input from the components of the detector unit 74. As the different TEM modes are orthogonal to each other and the optical ring resonator 69 may be configured to have different resonance frequencies, i.e., optical lengths, for different transversal electric modes, different resonant frequencies may be transmitted by the optical resonator and are then fed into optical wire 70, into mode splitter 71, one of the branches comprising a mode converter instead of the polarization rotator 72. An example for such a mode converter can be found in R. L. Eisenhart, "A Novel Wideband TM 01 to TM 11 Mode Converter", IEEE MTT-S Intl., Jun. 7-12, 1989, vol. 1, pages 249-252. Once the TM 01 mode is converted to a TM 11 mode, they may be coupled and superposed in the optical coupler 73.

The invention claimed is:

1. An optical sensor arrangement for measuring an observable comprising:

at least one light source for generating a first light component of a first frequency comprising a first mode and a second light component of a second frequency comprising a second mode orthogonal to said first mode;

an optical resonator having differing optical lengths for the first and second modes within a frequency interval including the first and second frequencies, at least one of the optical lengths being variable depending on the observable and a dependence of the respective optical length on the observable being different for said first and second modes, wherein the at least one light source is optically coupled to the optical resonator for feeding the first and second light components into the optical resonator, and the at least one light source comprises a first light source for generating the first light component and a second light source for generating the second light component, the first and second light sources being coupled to the optical resonator and being independently tunable of each other;

a detector unit being coupled to the optical resonator for coupling out the light components and being configured for detecting a frequency difference between a resonance frequency of the optical resonator for the first mode and a resonance frequency of the optical resonator for the second mode;

a mode converter arrangement situated between the optical resonator and the detector unit, the mode converter arrangement configured to rotate the first and/or second mode such that the modes comprise components in a matching direction; and a control unit for controlling the at least one light source and/or the optical resonator, the control unit configured such that a scan time through the entire frequency interval is different for the first and second light sources, and the scan time of the first light source is at least five times the scan time of the second light source.

2. The optical sensor arrangement of claim 1 wherein the control unit preferably tunes the at least one light source through said frequency interval.

3. The optical sensor arrangement of claim 1 wherein the mode converter arrangement is configured to rotate the first and/or second modes such that both modes comprise components in a matching transversal direction.

4. The optical sensor arrangement of claim 3 wherein the mode converter arrangement comprises a polarization rotator and a polarization splitter.

5. The optical sensor arrangement of claim 1 wherein the first and second modes are different polarizations of light or orthogonal TEM modes of light.

6. The optical sensor arrangement of claim 1 wherein the optical resonator is at least partially covered with an active layer of covering material for selectively adsorbing a group of substances comprising a substance to be detected and wherein the covering material is configured such that at least one of the resonance frequencies is shifted when the substance contacts the active layer.

7. The optical sensor arrangement of claim 1 wherein the detector unit comprises a photo detector and/or an electronic spectrometer and/or wherein the detector unit is configured for determining said frequency difference as a beat frequency of a superposition of the first light component and the second light component.

8. The optical sensor arrangement of claim 1 wherein the optical resonator is a ring resonator or a Fabry-Perot resonator.

9. The optical sensor arrangement of claim 1 wherein the at least one light source is coupled to the optical resonator through at least one optical path comprising an optical waveguide.

10. The optical sensor arrangement of claim 1 wherein a coupler is situated before or behind the optical resonator.

11. A method for measuring an observable by means of an optical sensor arrangement, the method comprising:
coupling light of a first light source of a first frequency comprising a first mode into an optical resonator;
coupling light of a second light source of a second frequency comprising a second mode into the optical resonator, wherein the second mode is orthogonal to the first mode and the optical resonator having differing optical lengths for the first and second modes within a frequency interval including the first and second frequencies, at least one of the optical lengths being variable depending on the observable and a dependence of the respective optical length on the observable being different for the first and second modes;
changing the first and second frequencies such that a scan time through an entire frequency interval is different for the first and second light sources, and the scan time of the first light source is at least five times the scan time of the second light source;
detecting a frequency difference between the resonance frequency of the first and second mode; and
coupling the light of the first and/or second frequency to a mode converter arrangement situated behind the optical resonator, the mode converter arrangement configured to rotate the first and/or second mode such that the modes comprise components in a matching direction.

12. The method of claim 11 wherein the light of the first and the light of the second frequency is coupled to the optical resonator simultaneously.

* * * * *